United States Patent [19]
Harper

[11] Patent Number: 6,156,694
[45] Date of Patent: Dec. 5, 2000

[54] RANEY COBALT CATALYST AND A PROCESS FOR HYDROGENATING ORGANIC COMPOUNDS USING SAID CATALYST

[75] Inventor: Mark Jay Harper, Middletown, Del.

[73] Assignee: E. I. Dupont De Nemours & Company, Wilmington, Del.

[21] Appl. No.: 09/186,839

[22] Filed: Nov. 5, 1998

[51] Int. Cl.[7] .............................. B01J 25/02; B01J 23/40; C07C 255/00; C07C 69/52; C07C 209/00

[52] U.S. Cl. .......................... 502/301; 502/326; 558/452; 558/459; 560/205; 562/598; 564/491; 568/382; 568/448

[58] Field of Search ..................................... 502/301, 326; 558/452, 459; 560/205; 562/598; 564/491; 568/382, 448

[56] References Cited

U.S. PATENT DOCUMENTS

| | | | |
|---|---|---|---|
| 2,257,814 | 10/1941 | Rigby | 260/464 |
| 4,544,749 | 10/1985 | Tadashi et al. | |
| 4,826,799 | 5/1989 | Cheng et al. | 502/301 |
| 4,895,994 | 1/1990 | Cheng et al. | 585/270 |
| 5,011,996 | 4/1991 | Kiel et al. | 564/321 |
| 5,151,543 | 9/1992 | Ziemecki | 558/459 |

FOREIGN PATENT DOCUMENTS

| | | |
|---|---|---|
| WO 96/18603 | 8/1996 | WIPO . |
| WO 97/37963 A1 | 4/1997 | WIPO . |
| WO 98/43941 | 10/1998 | WIPO . |

OTHER PUBLICATIONS

S.F. Chernyshov, Yu, I. Kryukov, and A.G. Pshenichnikov, Electrocatalytic Processes in Alkaline Electrolyzers, A.N. Frumkin Institute of Electrochemistry, 28, No. 3, 391–397, Mar. 1992.

D.V. Sokol'skii, T. Kh. Avetisyan, and A.S. Khlystov, Investigation of Skeletal Iron–Cobalt Catalysts by γ–Resonance (Mossbauer) Spectroscopy in the Course of Liquid–Phase Hydrogenation of Ethynyldimethylcarbinol Under Hydrogen Pressure, *Institute of Organic Catalysis and Electrochemistry, Academy of Sciences of the Kazakh SSR.*, 56, No. 1, Jan. 23–26, 1983.

*Primary Examiner*—Joseph McKane
*Assistant Examiner*—Joseph Murray
*Attorney, Agent, or Firm*—Shanks & Herbert

[57] ABSTRACT

The present invention relates to a Raney catalyst comprising iron, cobalt, a third metal wherein the third metal is selected from the group consisting of nickel, rhodium, ruthenium, palladium, platinum, osmium, iridium and mixtures of any of the metals of this group.

18 Claims, 2 Drawing Sheets

- ■ ACN
- ○ HMD
- —— Catalyst of Present Invention
- ---- Catalyst of Prior Art

RANEY COBALT CATALYST AND A PROCESS FOR HYDROGENATING ORGANIC COMPOUNDS USING SAID CATALYST

This invention concerns a novel Raney cobalt catalyst, its preparation and process for its use in the catalytic hydrogenation of unsaturated organic groups including those with carbon to carbon multiple bonds, oxygen containing groups and reducible nitrogen-containing groups, particularly nitrites. More specifically, but not by way of limitation, the present invention provides an improved catalyst and process for hydrogenation of adiponitrile (ADN) to 6-aminocapronitrile (ACN) and/or hexamethylenediamine (HMD).

BACKGROUND

U.S. Pat. No. 5,011,996 discloses Raney catalysts containing nickel and/or cobalt used in the presence of organic sulfur compounds to catalyze hydrogenation of reaction products of oxo compounds with amines or ammonia to the respective amines.

U.S. Pat. Nos. 4,826,799 and 4,895,994 are directed to catalysts made by the Raney process and pelletized in a matrix of polymer and plasticizer. Each makes a broad disclosure of Raney process alloys consisting of 45–75 weight % Al and 25–55% of a conventional Raney process metal, e.g., Ni, Co, Cu, or Fe, or mixture of these. Promoters may also be present such as Cr, Mo, Pt, Rh, Ru, Os, and Pd, typically at about 2 weight % of total metal.

U.S. Pat. No. 2,257,814 describes hydrogenation of dinitriles in the presence of mild-acting catalysts prepared by leaching an alloy of aluminum, iron and cobalt with an aqueous alkaline solution to provide the catalyst which contains 5% to 10% by weight of cobalt and 95% to 90% by weight of iron. The rate of hydrogenation of adiponitrile using this catalyst (as shown in Example 3B, below) is much too slow to provide a viable commercial process.

U.S. Pat. No. 5,151,543 reports a process for selective hydrogenation of aliphatic dinitriles to aminonitriles under low pressure with high yield using a Raney-type catalyst selected from the group consisting of Raney nickel, Raney cobalt, and Raney nickel promoted with metals or metal oxides selected from Group VIB or promoted with ferrous metals of Group VIII of the Periodic Table. Thus, in this catalyst, iron, if used at all, would be present in only low concentrations.

Sokol'skii, D. V., T. Kh. Avetisyan and A. S. Khlystov, Zh. Prikl. Khim. (Leningrad), 56 No. 1, pp 23–26 (1983). Raney-type cobalt-iron catalysts were prepared from alloys of the following compositions: 75Al—5Co—20Fe, 75Al—10Co—15Fe, 75Al—15Co—10Fe, and 75Al—20Co—5Fe. Variation of the phase composition and properties of these cobalt-iron catalysts were studied by Mossbauer spectroscopy during the hydrogenation of ethynyldimethylcarbinol. This publication did not disclose a combination of three metals used with aluminum to prepare Raney-type catalysts.

PCT/Fr95/01643 claims a process for the hemi-hydrogenation of aliphatic dinitriles using hydrogen in and a Raney nickel or; Raney cobalt catalyst, where the Raney nickel catalyst also contains a dopant chosen zinc and the elements of Groups IVb, Vb, VIb, VIIb and VIII of the Periodic Table, and where the Raney cobalt catalyst also contains a strong inorganic base and a dopant chosen zinc and the elements of Groups IVb, Vb, VIb, VIIb and VIII of the Periodic Table. It is also disclosed that the dopants usually represent from 0% to 15% and preferably from 0% to 10% of the weight of nickel or cobalt.

WO97/37963 discloses Raney catalysts for hydrogenation of compounds containing at least one unsaturated carbon-nitrogen bond. The catalysts contain cobalt and/or iron and can be modified with metals of Groups VIb (Cr, Mo, W) and VIII (Ru, Os, Rh, Ir, Pd, Pt) of the Periodic Table as well as Cu, Mn, and Re. The content of cobalt or iron in the catalyst is generally in the range of 50–99.9% by weight, preferably 80–99% by weight relative to the active components (cobalt and/or iron+modifying agent).

An object of the present invention is to provide a Raney catalyst having high selectivity, high reaction rates and long service lives. The presence of the small quantity of the third Group VIII metal in the Raney catalyst composition provides faster rates of hydrogenation than do catalysts consisting only of cobalt and iron. The ratio of iron to cobalt in these catalysts assures long reaction life.

A more specific object of this invention is to provide a Raney metal catalyst which has a low ingredient cost and is suitable for use in continuous operation to give a stable reaction rate and product selectivity in low temperature, low pressure hydrogenation of adiponitrile (ADN) to 6-aminocapronitrile (ACN) and/or hexamethylenediamine (HMD).

SUMMARY OF THE INVENTION

The present invention provides a Raney cobalt catalyst comprising cobalt, iron and a third metal wherein the third metal is selected from the group consisting of nickel, rhodium, ruthenium, osmium, iridium, platinum, palladium and mixtures of these metals and wherein the concentration of the cobalt in the catalyst on a dry basis is at least 30% but not more than about 70% by weight; the concentration of iron in the catalyst on a dry basis is from at least 5% to 40% by weight; the content of the third metal in the catalyst on a dry basis is from about 1% to not more than 6% by weight.

Nickel is the preferred third metal, and the preferred catalyst has the following metal concentrations: the concentration of the cobalt is about 50% by weight; the concentration of the iron is about 17% by weight; the concentration of the nickel is about 2% by weight.

The present invention includes a process for the hydrogenation of unsaturated organic compounds comprising contacting an unsaturated organic compound or contacting the unsaturated organic compound in the presence of a solvent with the Raney cobalt catalyst of the instant invention in the presence of hydrogen at a reaction pressure of from about 50 to about 2000 psig (0.34 to 13.8 MPa) and a reaction temperature of from about 25° C. to about 150° C.

This process is useful in hydrogenating unsaturated organic compounds comprising olefins, acetylenes, ketones, aldehydes, amides, carboxylic acids, esters of carboxylic acids, nitro compounds, nitriles, and imino compounds. This process is particularly useful in the hydrogenation of nitrites to primary amines, especially for the hydrogenation of adiponitrile.

The present process is useful at moderate conditions: a reaction pressure from about 50 to about 1000 psig (0.34 to 6.9 MPa) and a reaction temperature from about 25° C. to about 100° C.

The present process may be run as a continuous, semi-batch or as a batch process.

The catalyst of the present invention is prepared by treating an alloy of metals with alkali, the alloy comprising from 20% to 50% by weight cobalt, 3% to 30% by weight iron, 0.5% to 3% by weight of a third metal wherein the third metal is selected from the group consisting of nickel, rhodium, ruthenium, osmium, iridium, platinum, palladium, and mixtures of these metals with the remainder being an alkali-soluble metal selected from the group consisting of aluminum, zinc, magnesium and silicon. Nickel is the preferred third metal, and the preferred concentration range for the nickel is the range from 0.5% to 1.5%, and most preferred is a concentration of nickel of about 1%. A preferred composition of the alloy is cobalt about 24% to 34%, iron about 5% to 15% and nickel about 0.5% to 1% with the remainder being aluminum.

DETAILED DESCRIPTION OF THE INVENTION

Figure 1:
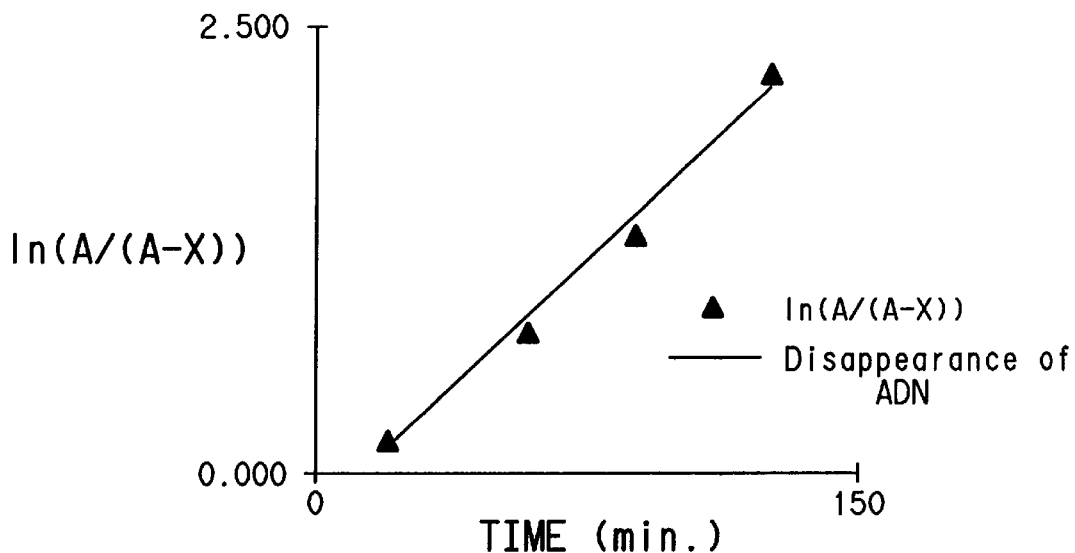
FIG. 1 shows data collected in Example 2 as a plot of the disappearance of ADN as a function of time compared to a first order rate line given by ln (A/(A–X).

The Raney cobalt catalysts of this invention are prepared by treating a metal alloy powder with an alkali, the composition of the metal alloy being by weight: 20% to 50% cobalt, 3% to 30% iron, 0.5% to 3% of a third metal wherein this third metal is selected from the group consisting of nickel, rhodium, ruthenium, osmium, iridium, platinum, palladium and mixtures of the metals of this group. The remainder of the alloy composition is a metal soluble in alkali. The alkali-soluble metals include aluminum, zinc, magnesium and silicon. Aluminum is the preferred alkali-soluble metal, and nickel is the preferred third metal for the catalyst.

The alloy from which the catalyst of the present invention is made, is prepared by the usual metallurgical procedures which produce alloy ingots. To obtain the alloy in the desired powder form, the ingot is crushed and ground. A sieved alloy powder having a particle size that will pass a 30 mesh screen is preferably used.

The alloy powder is converted to active catalyst by treatment with an aqueous alkali solution, preferably sodium hydroxide. This solution leaches out the majority of the aluminum or other alkali-soluble metal to yield the active Raney metal catalyst. The metal contents of the active catalysts of the present invention on a dry basis are by weight from about 30% to about 70% cobalt, from about 5% to about 40% iron, from about 1% to about 6% of a third metal wherein this third metal is selected from the group consisting of nickel, rhodium, ruthenium, osmium, iridium, platinum, palladium and mixtures of the metals of this group. The remainder of the catalyst composition depends on whether or not promoters have been added and on the thoroughness of the leaching process. Generally some small amount of the alkali-soluble metal, e.g. aluminum, will remain in the catalyst. The alkali-soluble metal residues may be present as oxides. The catalyst compositions according to the present invention, above, have been normalized to the oxide-free composition.

The catalysts of the present invention are used for promoting the reaction of hydrogen with organic compounds which contain unsaturated groups including olefinic; acetylenic; carbonyl in ketones, aldehydes, amides, carboxylic acids and esters; nitro; imino; and nitrile groups. These catalysts are particularly useful for hydrogenation of nitrites. For hydrogenation of nitrites, process costs are minimized because low pressure in the range of about 50 psig (0.34 MPa) to about 2000 psig (13.8 MPa) is used, and the hydrogenation proceeds well at temperatures from about 25° C. to about 150° C. However, the catalysts of this invention also function well at higher temperatures and pressures. The preferred range of pressure is from about 200 psig (1.4 MPa) to about 1000 psig (6.9 MPa) and that of temperature is from about 60° C. to about 90° C. Hydrogenations using catalysts of the present invention do not require the presence of caustic soda or other strong alkali.

Hydrogenation according to the present invention may be run in the presence of a solvent such as liquid ammonia, aqueous ammonia, an aliphatic alcohol having one to four carbon atoms or an aliphatic hydrocarbon having four to ten carbon atoms. The presence of one or more solvents can improve the selectivity to aminonitriles in the hydrogenation of dinitriles. In the hydrogenation of adiponitrile (ADN), solvents in amounts greater than one mole per mole of dinitrile may be used, and it is preferred to use from about one mole to about five moles of solvent per mole of ADN.

The process of the present invention may be operated batchwise, semibatchwise or continuously in an appropriate reactor. For commercial manufacture, the continuous process is preferred. In the hydrogenation of ADN to produce ACN and/or HMD the invention catalyst has a low deactivation rate and provides a stable reaction rate and distribution of products needed for a successful continuous commercial process.

Figure 3:
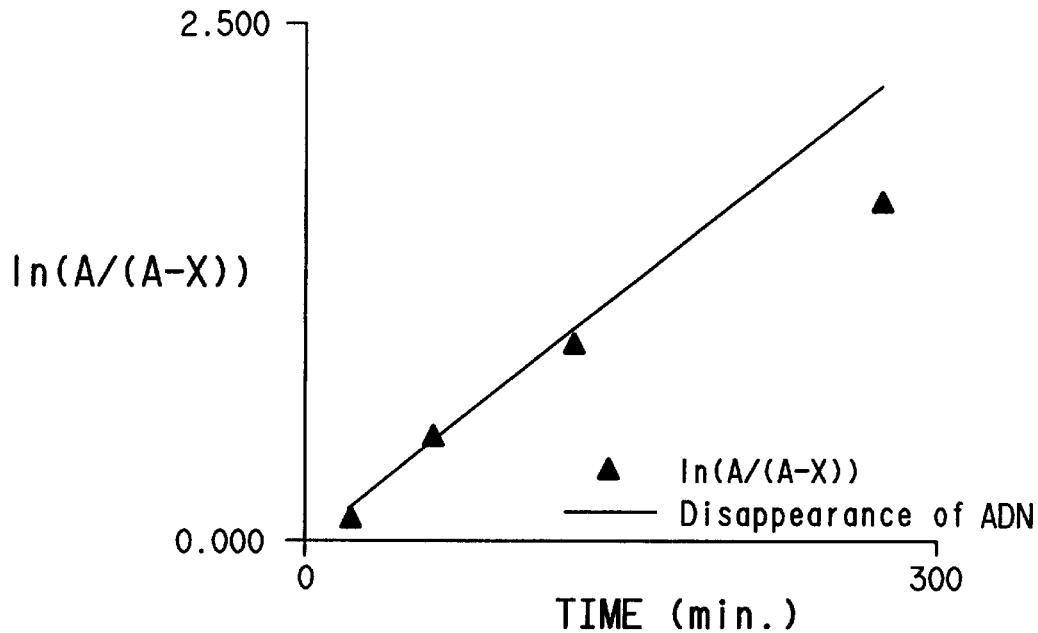
FIG. 3 shows a plot of the disappearance of ADN as a function of time, similar to FIG. 1, but illustrates an unstable catalyst. This plot is based on Example 7.

The stability of a catalyst for potential use in a continuous hydrogenation of a nitrile can be assessed from rate data generated in a semibatch reaction. Thus, in the hydrogenation of adiponitrile, the reaction follows a first order rate relationship. Negative deviation with time from the first order rate pattern indicates deactivation (loss of stability) of the catalyst activity. Experimentally, the first order rate line, which is equal to the natural log (ln) of the quantity (A/(A–X)) where A represents the initial mole concentration of reactant, A, and (A–X) represents the concentration of A at time t, and X is the mole concentration of products formed, is plotted using the least squares method based on the first few data points that are in a linear relationship. When the experimental data points, throughout the reaction, are a good fit to this first order rate line, the catalyst is stable and displays no deactivation as is illustrated in FIG. 1, but, when the plot of the experimental data points shows a negative deviation (decreasing slope), deactivation of the catalyst has occurred. Catalyst deactivation is shown in FIG. 3. The catalysts of the present invention show outstanding stability as is shown in the Examples below.

Reactors useful for performing the continuous hydrogenation according to the present invention include, generally, any conventional hydrogenation reactor. Examples of such reactors include, but are not limited to, plug flow reactor, continuous stirred tank reactor, and bubble column reactor. An example of a bubble column reactor, which is not confined to this reaction, has been described in U.S. Pat. No. 4,429,159. Descriptions of plug flow and continuous stirred tank reactors have been delineated in the book entitled "Chemical Reaction Engineering" written by Octave Levenspiel.

The continuous hydrogenation of adiponitrile described below in Example 4 was carried out in a continuous stirred tank reactor (CSTR) based on a 300cc autoclave designed and fabricated by Autoclave Engineers. It was constructed of Hastelloy-C with a maximum allowable working pressure of about 1500 psig (7.2 MPa) at 300° C. Mixing in the reactor was performed with a magnetically coupled impeller, mounted on a hollow shaft and driven by an electric motor. The reactor was heated with a 400 Watt external band heater.

Because they give long term stability without deactivation in continuous operation, the most preferred Raney metal catalysts of this invention are those prepared from alloys containing, by weight, from about 25% to about 45% cobalt, from about 4% to about 25% iron, from about 0.5% to about 2% nickel, with the remainder being aluminum. The limits on the nickel content are of particular importance since catalyst stability is lessened at higher nickel contents and reaction rate is slowed if the nickel is eliminated. The long term stability of the preferred catalyst composition made from an alloy containing 1% nickel is demonstrated by the continuous run of Example 4.

The present invention further provides a process for hydrogenation of an organic nitrile, comprising contacting the nitrile with gaseous hydrogen in the presence of a Raney cobalt catalyst prepared from a metal alloy containing by weight: 20% to 50% cobalt, 3% to 30% iron, 0.5% to 2% of a third metal wherein the third metal is selected from the group consisting of nickel, rhodium, ruthenium, osmium, iridium, platinum, palladium, and mixtures of metals of this group with the remainder being an alkali-soluble metal selected from the group consisting of aluminum, zinc, magnesium and silicon.

Although low pressure is preferred for the process of the present invention, the process may be run at higher pressures. Pressures of more than 2000 psig (13.8 MPa) can be used with the process and catalyst of this invention, but such high pressures may not be cost effective.

The following Examples illustrate the present invention, but are not intended to limit the invention.

EXAMPLE 1
Preparation of the Catalyst of the Present Invention

Into a graphite crucible was placed 54.20 g of aluminum. The crucible was then placed in a quartz cup which was partially filled with popcorn quartz for insulation. The quartz cup with its contents was positioned inside the coil of an induction furnace. When the aluminum was melted, a mixture of 9.03 g iron chips, 26.20 g cobalt chips and 0.90 g nickel shot was carefully added to the molten aluminum from a 100 ml porcelain addition cup. The resulting molten mixture was stirred with a graphite rod. The furnace was closed, and the power turned on for 2 minutes. The furnace was opened, the melt was again stirred with the graphite rod, the furnace closed again, and the power was applied for another 2 minute period. The power to the furnace was then turned off, and the furnace was opened. The graphite crucible with its molten contents was lifted from the quartz cup, and the molten metal alloy was poured from the graphite crucible onto a graphite cooling plate located inside the furnace. After the alloy had cooled and hardened for about 10 minutes, it was removed from the graphite cooling plate and cooled under water until it was at room temperature.

The cooled alloy was dried, crushed to provide pieces less than 5 mm in their longest dimension and milled using one inch diameter steel balls in a planetary ball mill. The milled powder was screened using a 30 mesh sieve. The screened alloy powder was stored in a labeled container and was ready for activation. Based on the metals charged the composition of the alloy was by weight 60% aluminum, 29% cobalt, 10% iron, and 1% nickel.

The alloy was converted to active Raney metal catalyst by leaching most of the aluminum from the alloy with dilute aqueous sodium hydroxide at 80° C. to 90° C. The resulting catalyst was separated by decantation from the alkline solution and washed repeatedly with deionized water until the pH was less than 7.5. The activated catalyst was stored under water at pH 9.

The catalyst when dried contained 50.5% cobalt, 16.5% iron, 1.9% nickel and 2.4% aluminum.

EXAMPLE 2
Hydrogenation of Adiponitrile

A 100 ml Hastelloy-C Parr stirred autoclave was used for the hydrogenation. The autoclave reactor cup was charged with 1.0 g of wet catalyst (0.5 g on a dry basis), prepared by the procedure of Example 1, and 26.2 g of 30% aqueous ammonium hydroxide. The reactor cup was secured to the reactor head, and the reactor was leak-tested with 300 psig (2.1 MPa) nitrogen and then purged with hydrogen. After the reactor contents were heated to 75° C. under 200 psig (1.4 MPa) hydrogen pressure, a mixture of 10.8 g adiponitrile, 5.0 g methanol and 0.5 g 1-methyl-2-pyrrolidinone (NMP) was injected from a 75 ml addition cylinder under 500 psig (3.4 MPa) hydrogen pressure (the NMP was added as an internal standard for GC analysis). The temperature of 75° C. and hydrogen pressure of 500 psig (3.4 MPa) were maintained until hydrogen takeup was 117 psig (0.81 MPa) as measured from a 500 ml hydrogen supply reservoir. The reaction time was 127 minutes. During the hydrogenation, periodic samples (0.5 ml) were withdrawn from the reactor and analyzed by GC in order to construct concentration profiles of the main reaction components.

The GC analysis data showed that the ADN conversion was 90% at 127 minutes. At 75% ADN conversion, 54% ACN and 14% HMD had formed; selectivity (defined as in Mares, et al, J. Catal., 112, 145–156, 1988) to ACN was 72%. Byproduct concentration at 75% ADN conversion was about 6%; the byproducts comprised bishexamethylenetriamine and traces of hexamethyleneimine and tetrahydroazepine. The first order reaction rate constant was 1.165 hr$^{-1}$. As shown in FIG. 1, the data points for the first order ADN disappearance compared to the first order rate line indicated good catalyst stability.

EXAMPLE 3A and 3B To Be Compared to Example 2

The following two comparative examples show the slow rate of hydrogenation when using a catalyst containing cobalt and iron but not the third metal as is required by the present invention.

3A. Hydrogenation of Adiponitrile

Using the procedure of Example 1, an alloy consisting of, by weight, 60 parts aluminum, 30 parts cobalt and 10 parts iron was prepared. This alloy was pulverized and converted to active Raney metal catalyst by treatment with aqueous sodium hydroxide.

The semibatch reactor procedure as described in Example 2 was used with 1.0 g of the above wet catalyst, 26.2 g of 30% aqueous ammonium hydroxide, 10.8 g adiponitrile, 0.5 g NMP, and 5.0 g methanol.

Figure 4:
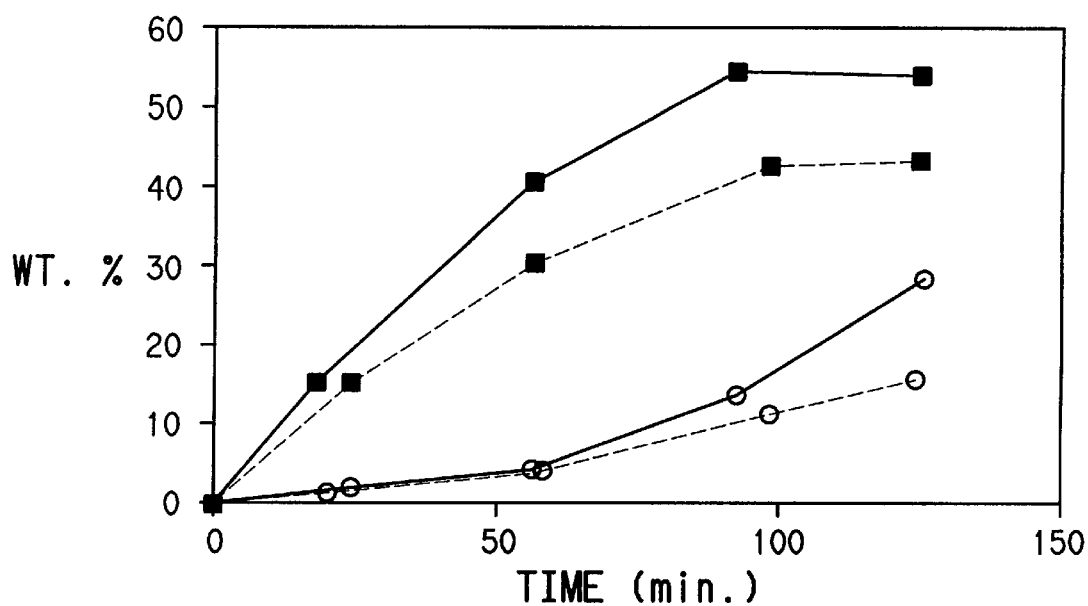
FIG. 4 shows a comparison the rate of reaction (production of ACN and HMD in weight %) of a catalyst of the present invention (A) with that of the prior art (B).

The hydrogenation was conducted at 75° C. under a pressure of 500 psig (3.4 MPa) until the hydrogen uptake was 139 psig (0.96 MPa) as measured from a 500 ml hydrogen supply reservoir. Reaction time was 330 min. The reaction mixture was analyzed by GC. ADN conversion was 89% at 208 min. at which time 45% ACN, 29% HMD and 7% byproducts had formed. Selectivity to ACN was 56%. The first order reaction rate constant was 0.674 hr$^{-1}$. The rate of ACN and of HMD formation for this Example (catalyst B) vs. that of reaction of Example 2 (catalyst A) is shown in the plots of FIG. 4.

3B. Hydrogenation of Adiponitrile

An alloy containing by weight 60 parts of aluminum, 38 parts of iron, and 2 parts of cobalt was prepared and was treated with aqueous sodium hydroxide to give the activated catalyst as described in Example 1 of U.S. Pat. No. 2,257,814.

ADN was hydrogenated in the presence of this activated catalyst according to the reactor procedure of Example 2. This hydrogenation produced ACN and HMD, but the reaction rate was much slower than that observed in Example 2. The first order rate constant was only 0.088 hr$^{-1}$ while with the invention catalyst it was 1.165 hr$^{-1}$. After a reaction time of 303 minutes, ADN conversion was only 34% while with the invention catalyst of Example 1, ADN conversion was 95% after only 127 minutes.

ADN and ammonia were then each continuously added to the reactor using ISCO syringe pumps. Rate of addition of ADN was 18 ml per hour and that of the ammonia was 12 ml per hour. Simultaneously, water was added at a rate of 1.0 ml per hour. Hold up time of the products in the reactor was 4.0 hours.

Figure 2:
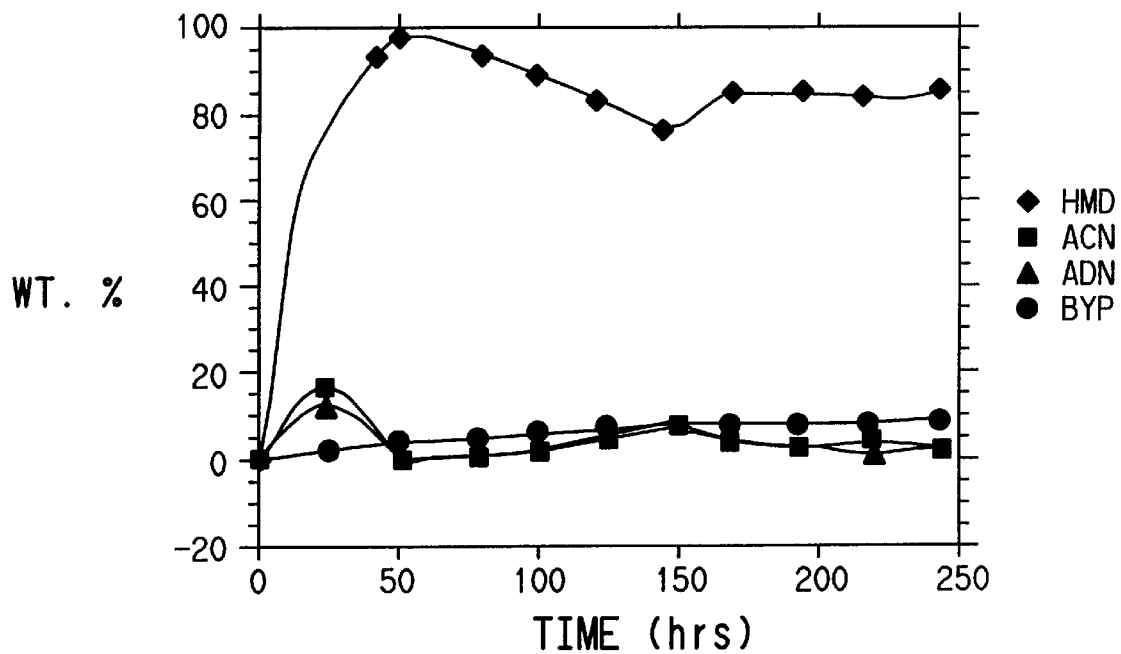
FIG. 2 shows the product distribution of the continuous run described in Example 4.

Product was collected in a one liter product receiver which was connected to the reactor through a let-down tank. As the reaction proceeded, samples were taken at regular intervals and analyzed by GC for ACN, HMD, ADN and byproducts (BYP). The analytical results showing the production of ACN, HMD, and BYP are listed in Table 1 and are shown graphically in FIG. 2.

The continuous hydrogenation proceeded in a stable manner for 240 hours (10 days), the end of the experimental run. Both ACN and HMD were produced in uniform yields with HMD being the major product.

TABLE 1

Continuous Hydrogenation of ADN

| TOS (hr) | g ADN/ g Catalyst | Temp. (° C.) | Pressure (psig) | HMD (%) | ACN (%) | ADN (%) | Byproducts (%) | HMD Produced (g) |
|---|---|---|---|---|---|---|---|---|
| 10 | 0.0 | 75 | 1000 | 0.0 | 0.0 | 0.0 | 0.0 | 0.0 |
| 20 | 46.4 | 75 | 1000 | 74.7 | 14.6 | 11.3 | 1.2 | 260.3 |
| 44 | 102.2 | 75 | 1000 | 94.4 | 2.6 | 2.3 | 2.5 | 654.9 |
| 48 | 111.5 | 75 | 1000 | 97.2 | 0.0 | 0.0 | 3.8 | 722.6 |
| 72 | 167.2 | 75 | 1000 | 97.1 | 0.0 | 0.0 | 4.0 | 1128.4 |
| 99 | 229.9 | 75 | 1000 | 91.0 | 2.7 | 2.4 | 4.9 | 1556.5 |
| 120 | 278.7 | 75 | 1000 | 83.4 | 5.3 | 4.2 | 6.5 | 1861.7 |
| 143 | 332.1 | 75 | 1000 | 77.4 | 8.7 | 7.0 | 7.5 | 2171.8 |
| 167 | 387.8 | 75 | 1000 | 85.0 | 3.9 | 3.9 | 8.2 | 2526.9 |
| 192 | 445.9 | 75 | 1000 | 84.9 | 3.2 | 2.5 | 8.0 | 2896.6 |
| 216 | 501.6 | 75 | 1000 | 84.2 | 3.8 | 1.6 | 8.4 | 3248.3 |
| 240 | 557.3 | 75 | 1000 | 86.3 | 2.1 | 2.0 | 8.7 | 3609.2 |

Notes:
TOS = Time on Stream
Holdup Time = 4.0 hrs.
Catalyst Charge = 7.5 g dry
Raney Catalyst from the alloy: 60% Al, 29% Co, 10% Fe, 1% Ni

EXAMPLE 4

This example illustrates the continuous hydrogenation of ADN.

A 300 cc continuous stirred tank reactor was used. It was provided with a thermocouple insert, rupture disc, and two ⅛ inch dip legs fitted with 5 micron stainless steel frits, designed for liquid addition into the reactor and product withdrawal from the reactor, respectively.

The reactor was charged with 120 grams of methanol, 0.6 ml 50% sodium hydroxide, and 15 grams of the wet activated catalyst (7.5 grams dry weight) of Example 1.

The reactor was sealed, flushed with nitrogen several times and leak-tested at 1000 psig (6.9 MPa). After ensuring that there were no leaks, the reactor contents were heated to 75° C. and the agitator switched on (1200 rpm). As soon as the desired reaction temperature of 75° C. was achieved, the reactor pressure was set to 1000 psig (6.9 MPa) by adjusting the back pressure regulator, and hydrogen was fed via the hollow shaft of the agitator. Hydrogen flow rate into the reactor was metered and monitored by a BROOKS mass flow controller. The hydrogen flow rate was set to 600 standard cubic centimeters per minute.

EXAMPLE 5

Hydrogenation of n-Butyronitrile

Using the procedure of Example 1, an alloy consisting of, by weight, 60 parts aluminum, 26 parts cobalt, 13 parts iron and 1 part of nickel was prepared. This alloy was pulverized and converted to active Raney metal catalyst by treatment with aqueous sodium hydroxide.

The semibatch reactor procedure as described in Example 2 was used with 1.0 g of the above wet catalyst, 26.2 g of 30% aqueous ammonium hydroxide, 10.8 g n-butyronitrile, 0.5 g NMP, and 5.0 g methanol. The hydrogenation was conducted at 75° C. under a pressure of 500 psig (3.4 MPa) until (345 min.) the hydrogen uptake was 126 psig (0.87 MPa) as measured from a 500 ml hydrogen supply reservoir. Analysis of the reaction mixture by GC showed a yield of 87% n-butylamine along with 5% di(n-butyl)imine as byproduct. The first order reaction rate constant was 0.394 hr$^{-1}$. The reaction rate followed the first order rate line through about 75% conversion of the n-butyro-nitrile and then showed a positive deviation (indicative of very good catalyst stability) over the remainder of the reaction.

EXAMPLE 6
Hydrogenation of Adiponitrile

ADN was hydrogenated according to the procedure of Example 2 using the catalyst of Example 5. The reaction conditions of 75° C. and 500 psig (3.4 MPa) hydrogen pressure were maintained until hydrogen uptake was 126 psig (0.87 MPa) as measured from a 500 ml hydrogen supply reservoir. The reaction time was 379 minutes at which time ADN conversion was 99%. At 72% ADN conversion, 48% ACN and 11% HMD had formed along with 4% byproducts. No catalyst deactivation was observed as indicted by a stable reaction rate following the first order rate line for disappearance of ADN. This is shown by the straight line plot of ln(A/A−X) vs. reaction time. In the expression ln(A/A−X), where X is the weight % of converted ADN at time t and A is the weight % (usually 100) of the ADN at time 0. The first order reaction rate constant was 0.613 hr$^{-1}$.

EXAMPLE 7
Hydrogenation of Adiponitrile

Using the procedure of Example 1, an alloy consisting of, by weight, 60 parts of aluminum, 27 parts of cobalt, 10 parts iron, and 3 parts nickel was prepared. This alloy was pulverized and converted to active Raney metal catalyst by treatment with aqueous sodium hydroxide.

Adiponitrile was hydrogenated using the above catalyst according to the procedure of Example 2. The reaction conditions of 75° C. and 500 psig (3.4 MPa) hydrogen pressure were maintained until hydrogen uptake was 86 psig (0.59 MPa) as measured from a 500 ml hydrogen supply reservoir. The reaction was stopped after 275 minutes at which time ADN conversion was 82%. At 62% ADN conversion, 44% ACN and 7% HMD had formed along with 3% byproducts. Catalyst deactivation was indicated starting at about 120 minutes of reaction time. This deactivation is shown by the decreasing slope (FIG. 3) of the plot of ln(A/A−X) vs. reaction time as compared to the first order line. The first order rate constant was 0.513 hr$^{-1}$.

EXAMPLE 8
Hydrogenation of Adiponitrile

Using the procedure of Example 1 an alloy consisting of, by weight, 60 parts aluminum, 25 parts cobalt, 10 parts iron, and 5 parts nickel was prepared. This alloy was pulverized and converted to active Raney metal catalyst by treatment with aqueous sodium hydroxide.

ADN was hydrogenated using the above catalyst according to the procedure of Example 2. The reaction conditions of 75° C. and 500 psig (3.4 MPa) hydrogen pressure were maintained until hydrogen uptake was 84 psig (0.58 MPa) as measured from a 500 ml hydrogen supply reservoir. The reaction was stopped after 174 minutes at which time ADN conversion was 71%. At 71% ADN conversion, 51% ACN and 12% HMD had formed along with 4% byproducts. Catalyst deactivation was noted starting at about 100 minutes of reaction time. This deactivation is shown by the decreasing slope of the plot of ln(A/A−X) vs. reaction time as compared to the first order rate line. The first order rate constant was 0.489 hr$^{-1}$.

What is claimed is:

1. A Raney cobalt catalyst comprising cobalt, iron and a third metal wherein the third metal is selected from the group consisting of nickel, rhodium, ruthenium, palladium, platinum, osmium, iridium or a combination of any of these metals and wherein the concentration of the cobalt in the catalyst on a dry basis is at least 30% but not more than about 70% by weight; the concentration of the iron in the catalyst on a dry basis is from at least 5 to 40% by weight; the content of the third metal in the catalyst on a dry basis is from about 1 to not more than 6% by weight.

2. A Raney cobalt catalyst comprising cobalt, iron and nickel, wherein the concentration of the cobalt in the catalyst on a dry basis is at least 30% but nor more than about 70% by weight; the concentration of the iron in the catalyst on a dry basis is from at least 5 to 40% by weight; and the content of the nickel in the catalyst on a dry basis is from about 1 to not more than 6% by weight.

3. The catalyst of claim 2 wherein the concentration of the cobalt is about 50% by weight; the concentration of the iron about 17% by weight; the concentration of the nickel is not more than about 2% by weight.

4. A process for the hydrogenation of unsaturated organic compounds comprising contacting the unsaturated organic compound or contacting the unsaturated organic compound in the presence of a solvent with a Raney cobalt catalyst according to claim 1 in the presence of hydrogen at a reaction pressure of from about 50 to about 2000 psig (0.345 to 13.78 MPa) and a reaction temperature of from about 25 to 150° C.

5. The process of claim 4 wherein the unsaturated organic compound is selected from the group consisting of olefins, acetylenes, ketones, aldehydes, amides, carboxylic acids, esters of carboxylic acids, nitro compounds, nitrites, and imino compounds.

6. The process of claim 4 where in the unsaturated organic compound is a nitrile.

7. The process of claim 4 wherein the reaction pressure is from about 50 to about 1000 psig (0.345 to 13.78 MPa) and a temperature of from about 60 to about 90° C.

8. The process of claim 4 wherein the process is continuous.

9. The process of claim 4 wherein the solvent is selected from the group consisting of liquid ammonia, aqueous ammonia, an aliphatic alcohol having one to four carbon atoms and an aliphatic hydrocarbon having four to ten carbon atoms.

10. The process of claim 4 wherein the process is batch or semi-batch.

11. The process of claim 6 wherein the nitrile is adiponitrile.

12. A Raney metal catalyst prepared by treating an alloy of metals with alkali, the alloy comprising from 20 to 50% by weight cobalt, 3 to 30% by weight iron, 0.5 to 3% by weight of a third metal wherein this third metal is selected from the group consisting of nickel, rhodium, ruthenium, palladium, platinum, osmium, iridium and mixtures of any of these metals and wherein the remainder of the mixture is an alkali soluble metal selected from the group consisting of aluminum, zinc, magnesium and silicon.

13. The catalyst of claim 12 wherein the third metal is nickel.

14. The catalyst of claim 12 wherein the concentration of the third metal is from 0.5 to 1.5%.

15. The catalyst of claim 12 wherein the concentration of the third metal is about 1%.

16. The catalyst of claim 12 wherein the concentrations are cobalt about 24 to 34%, iron about 5 to 15% and nickel about 0.5 to 1%.

17. A process for the hydrogenation of unsaturated organic compounds comprising contacting the unsaturated organic compound or contacting the unsaturated organic compound in the presence of a solvent with a Raney cobalt catalyst according to claim 2 in the presence of hydrogen at a reaction pressure of from about 50 to about 2000 psig (0.345 to 13.78 MPa) and a reaction temperature of from about 25 to 150° C.

18. The process of claim 17, wherein the concentration of nickel is not more than about 2% by weight.

* * * * *